United States Patent [19]
Schnirman

[11] Patent Number: 4,602,629
[45] Date of Patent: Jul. 29, 1986

[54] COMBINED SURGICAL BLADE AND CLIPS APPLICATOR

[76] Inventor: Gilbert A. Schnirman, 4001 NW 94th Ter., Coral Springs, Fla. 33065

[21] Appl. No.: 588,906

[22] Filed: Mar. 12, 1984

[51] Int. Cl.⁴ .............................................. A61F 17/32
[52] U.S. Cl. ..................................... 128/305; 128/346
[58] Field of Search ............... 128/305, 346, 325, 326, 128/334 R

[56] References Cited

U.S. PATENT DOCUMENTS

| | | | |
|---|---|---|---|
| 2,524,337 | 10/1950 | Whittaker | 128/305 |
| 3,106,919 | 10/1963 | Churchville | 128/346 |
| 3,175,556 | 3/1965 | Wood et al. | 128/305 |
| 3,631,858 | 1/1972 | Ersek | 128/346 |
| 4,026,294 | 5/1977 | Mattler | 128/305 |
| 4,046,148 | 9/1977 | Meador | 128/305 |
| 4,449,530 | 5/1984 | Bendel et al. | 128/325 |

Primary Examiner—John J. Wilson
Attorney, Agent, or Firm—Joseph Zallen

[57] ABSTRACT

A device is described for ligating a selected section of a blood vessel and then dividing the section. It comprises a resilient, flexible holder. The holder has a first portion foldable on to a second portion. A pair of foldable surgical clips is spaced apart in the holder but not permanently attached. Cutting means are attached to said first holder portion between said clips. Pressing said first and second holder portions together on a section of a blood vessel or the like, causes each said clip to clamp on to said blood vessel and then the cutting means to divide said blood vessel. When pressure is released on said holder, the holder and cutting means are retracted from said blood vessel leaving the clips in ligated position on the vessel.

7 Claims, 8 Drawing Figures 4,602,629

COMBINED SURGICAL BLADE AND CLIPS APPLICATOR

BACKGROUND OF INVENTION

One of the common procedures in surgery is the dividing of a blood vessel or other tubular structure (ie. vas deferens) and the ligating of its severed ends. One conventional method is to apply a clip to each of the two portions to be ligated and then sever the portion between the clips with a blade. There are a variety of clips on the market of various structure, size, and material; permanent and absorbable. All of these require either the individual consecutive separate manipulations of clipping and cutting with a blade, or the use of very specialized, expensive, cumbersome instruments for activating the clipping and cutting mechanisms.

Prior art relating to this invention includes the following U.S. Pat. Nos. and publication: 2,524,337; 3,106,919; 4,026,294 and 4,046,148 and LDS (described on pages 103-107 in "Stapling in Surgery" by F. M. Steichen and M. M. Ravitch, Year Book Medical Publishers, Chicago, Ill. 1984). None of these patents or publication teach or suggests the invention as explained below.

One object of the present invention is to provide a novel device which is disposable, sterilized and individually packaged, and which permits the surgeon to more easily, more rapidly and more inexpensively ligate and divide a blood vessel during a surgical procedure.

Other objects and advantages of this invention will be apparent from the specification and claims which follow, taken together with the appended drawings.

SUMMARY OF INVENTION

The invention comprises generally a resilient holder having cooperable portions foldable on one another. A pair of spaced surgical clips are seated in, but not permanently attached to the holder, and a blade permanently attached to one portion. When the surgeon, using a common ordinary surgical clamp, applies this device to a blood vessel the two holder portions close together causing the surgical clips to close irreversibly on to the blood vessel, followed by the blade dividing the blood vessel. Upon release of the pressure the holder springs open and is released from the blood vessel leaving the clips in position on the blood vessel.

No special tools are necessary in manipulating the devices of this invention since ordinary, surgical clamps may be used. Manipulation is simple and within the ordinary skill of the surgeon. The cutting means is preferably a knife blade but can also be a pair of shearing blades. Substantially any type of surgical clip permanent or absorbable can be used in this invention including wire clips. The devices, being quite inexpensive as compared with the prior art, permit stocking by the surgeon of different sizes to accommodate the length and diameter of the section to be ligated. With the use of a pair of spaced blades in the holder a desired length of tissue can be excised for pathological examination in addition to ligating.

SPECIFIC EXAMPLES OF INVENTION

Figure 1:
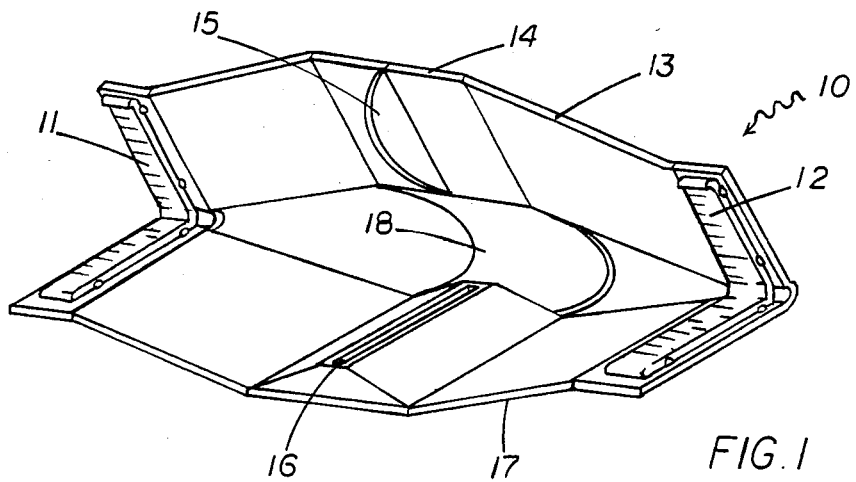
FIG. 1 is a perspective view of one embodiment of this invention in initial open condition.
Figure 2:
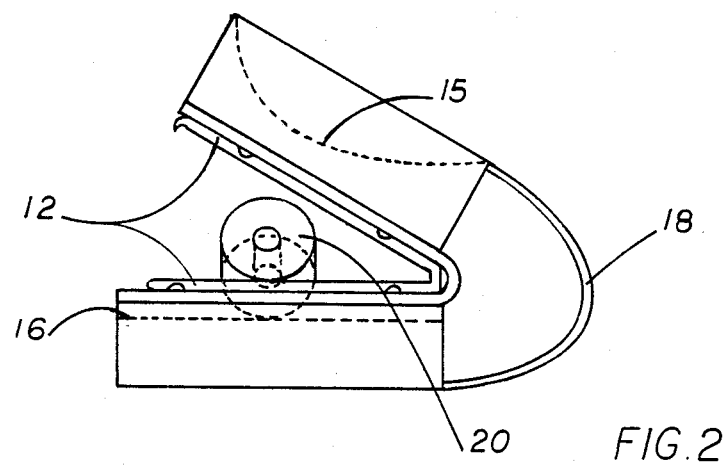
FIG. 2 is a side view of FIG. 1 showing the position of a blood vessel before operation of the device.
Figure 3:
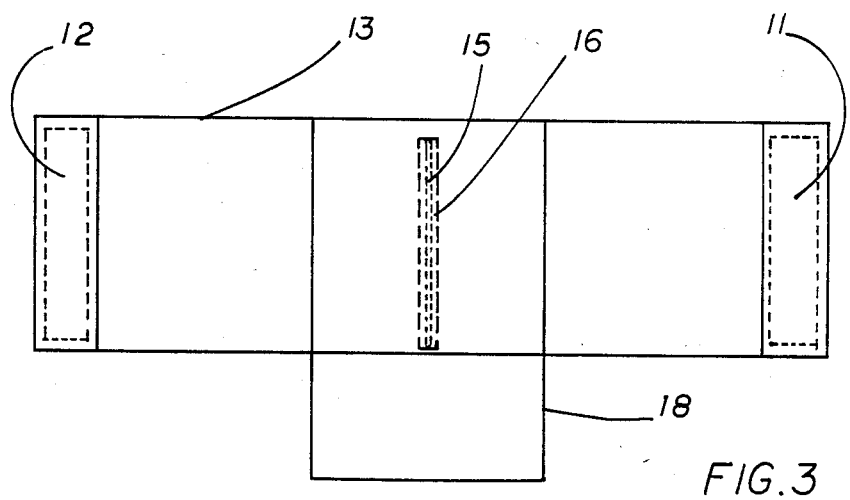
FIG. 3 is a top view.
Figure 4:
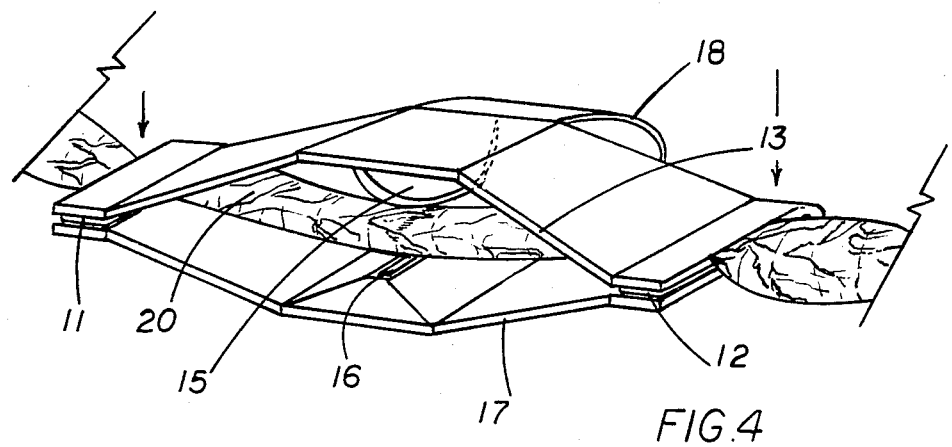
FIG. 4 is a perspective view of the device in position on a blood vessel showing the vessel uncut but ligated.
Figure 5:
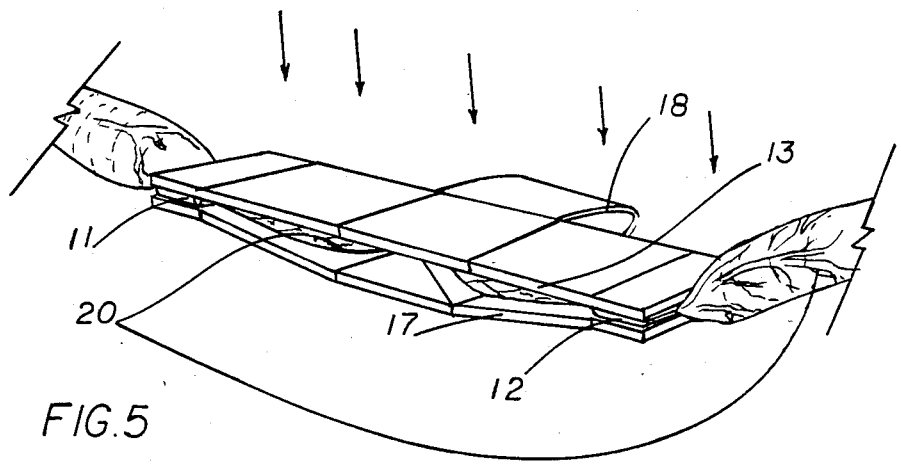
FIG. 5 shows the device in full closure on a blood vessel both ligated and divided.

Referring now to FIGS. 1 to 5 and 8, there is illustrated therein an embodiment 10 of this invention, including a holder 13 having upper portion 14 and lower portion 17 connected by resilient portion 18. Spaced at the ends of the holder are surgical clips 11 and 12 which seat in those ends but are not permanently attached to the holder. The upper portion 14 of the holder contains a vertical blade 15 while the lower portion 17 of the holder contains a blade receiving slot 16. The blade 15 is higher than clips 11 and 12 so that as a surgical clamp applies pressure on the upper and lower portions of the holder the clips 11 and 12 close irreversibly on the blood vessel 20 and then the blade 15 cuts through the portion of the blood vessel between the clips. When the pressure is released by the surgical clamp the spring portion 18 of the holder 13 causes the upper and lower portions 13 and 17 to reopen, the knife blade 15 to retract upwardly and the entire holder to come away from the blood vessel (FIG. 8) and be thrown away.

Figure 6:
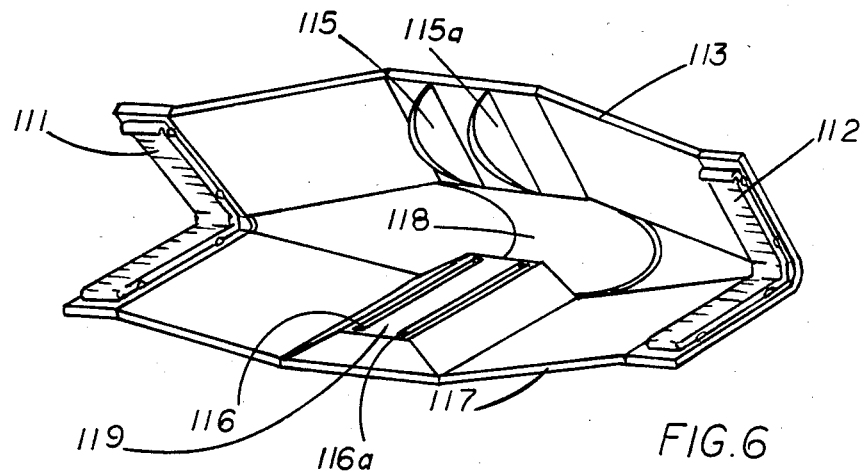
FIG. 6 is a perspective view of a second embodiment of this invention wherein two blades are provided so that a section of desired length can be removed as in a vasectomy to provide a surgical specimen.

The embodiment illustrated in FIG. 6 is of a similar construction and action except that it has two parallel vertical blades 115 and 115a on upper portion 114 of holder 113 and two receiving slots 116 and 116a on the lower portion 117 of the holder 113. The clips 111 and 112 are of similar construction as clips 11 and 12 in the previous example and the spring portion 118 has a similar resiliency as the spring portion 18. The clips 111 and 112 act irreversibly to hold on the blood vessel and then the blades cut through the blood vessel or other tubular tissue. The blades are then retracted upon release of pressure of the surgical clamp on the holder.

Figure 7:
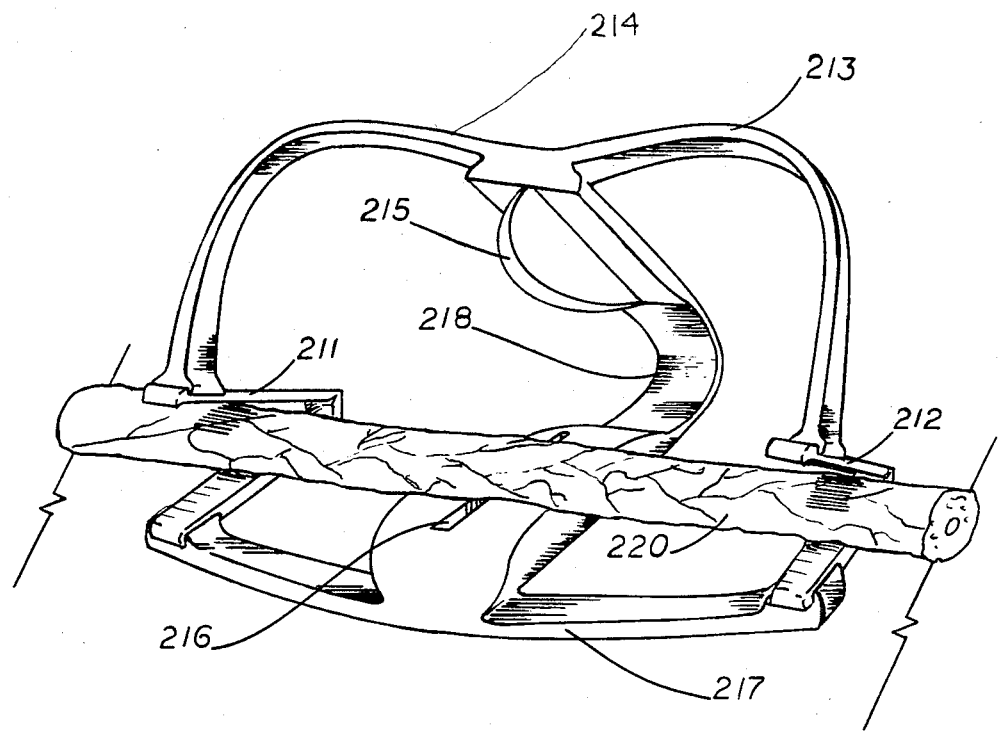
FIG. 7 is a perspective view of another embodiment of this invention shown in position to be applied to a blood vessel.
Figure 8:
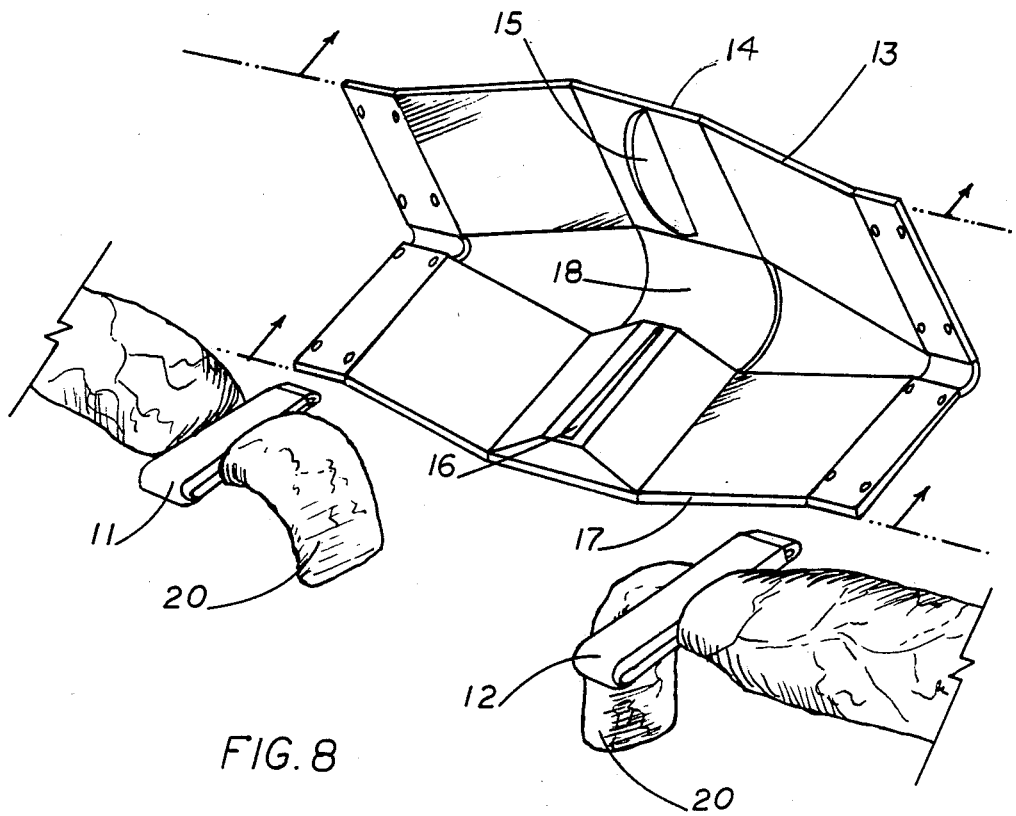
FIG. 8 is a view of the embodiment of FIG. 1 to 5 showing the holder removed from the divided, ligated blood vessel leaving a cuff of vessel past each clip.

The embodiment illustrated in FIG. 7 is a variation which is very open and contains less material and thus has greater visibility for the surgeon. The holder 213 comprises a strip-like upper member 214 and strip-like lower member 217 held together by a resilient means 218. Clips 211 and 212 are positioned so as to be able to engage blood vessel 220. Knife blade 215 is in a plane above the clips. It cuts the vessel 220 and extends into slot 216 after the clips have been irreversibly engaged around the blood vessel. Upon release of pressure from the surgical clamp the holder 213 comes away leaving the ligated and divided blood vessel.

I claim:

1. An integral surgical device for ligating a selected section of a blood vessel or the like and then dividing the section; said device comprising:
   (a) a resilient, flexible holder having a first portion foldable on to a second portion;
   (b) a pair of foldable surgical clips spaced apart in said holder but not permanently attached so that one portion of each said clip abuts said first holder portion and the other portion of each said clip abuts said second holder portion; and (c) cutting means attached to said first holder portion between said clips;

said device being characterised in that pressing said first and second holder portions together on a section of a blood vessel or the like, causes each said clip to clamp on to said blood vessel and then the cutting means to divide said blood vessel, and when pressure is released on said holder, said holder and cutting means are retracted from said blood vessel leaving the clips in ligated position on the vessel.

2. The device of claim 1 wherein said cutting means comprises a blade.

3. The device of claim 1 wherein said cutting means comprises a pair of spaced blades.

4. The device of claim 1 wherein said first and second holder portions are connected by a resilient portion.

5. The device of claim 1 which is disposable, and presterilized.

6. The device of claim 1 adapted for use with an ordinary surgical clamp.

7. The device of claim 1 further characterized in that the cutting means comprises a blade which is higher than the clips so that as a surgical clamp applies pressure on the upper and lower portions of the holder the clips first close on the blood vessel and then the blade cuts through the portion of blood vessel between the clips.

* * * * *